United States Patent [19]
Baker et al.

[11] Patent Number: 5,480,901
[45] Date of Patent: Jan. 2, 1996

[54] METHOD FOR REDUCING UNWANTED CELLULAR ADHESIONS

[75] Inventors: Margaret A. Baker, Philadelphia; Betsy M. Ohlsson-Wilhelm, Berwyn, both of Pa.

[73] Assignee: Zynaxis, Inc., Malvern, Pa.

[21] Appl. No.: 320,189

[22] Filed: Oct. 7, 1994

[51] Int. Cl.$^6$ .................................................. A01N 43/38
[52] U.S. Cl. ............................................................ 514/419
[58] Field of Search ............................................... 514/419

[56] References Cited

FOREIGN PATENT DOCUMENTS 9422468  10/1994  WIPO .

OTHER PUBLICATIONS

Carlson R et al Org. Mass Spectrom, (1994) 29(11) 632–40.
Spink, C et al Biochem, Biophys. Acta (1994) 1191(1) 164–72.
DeClerck, L. et al J. Immunol Methods (1994) 172(1) 115–24.

*Primary Examiner*—Paul J. Killos
*Attorney, Agent, or Firm*—Dann, Dorfman, Herrell and Skillman

[57] ABSTRACT

A conjugate comprising a drug which has an inhibitory effect on cellular adhesion and a lipophilic cell binding agent, when applied to a compromised site, e.g., due to surgical intervention, injury, chemotherapy, disease or inflammation, is effective in reducing unwanted adhesion formation.

34 Claims, 4 Drawing Sheets

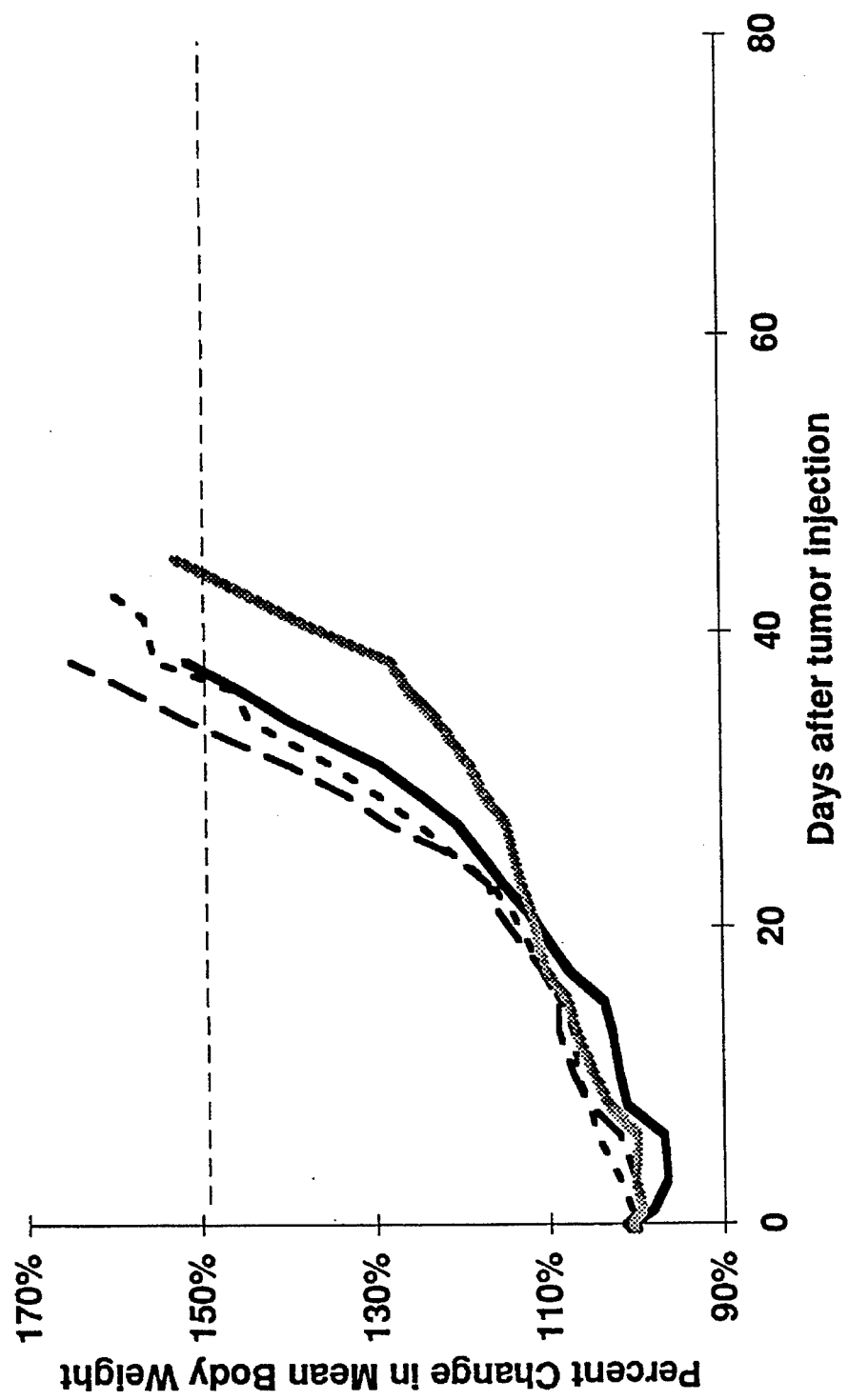

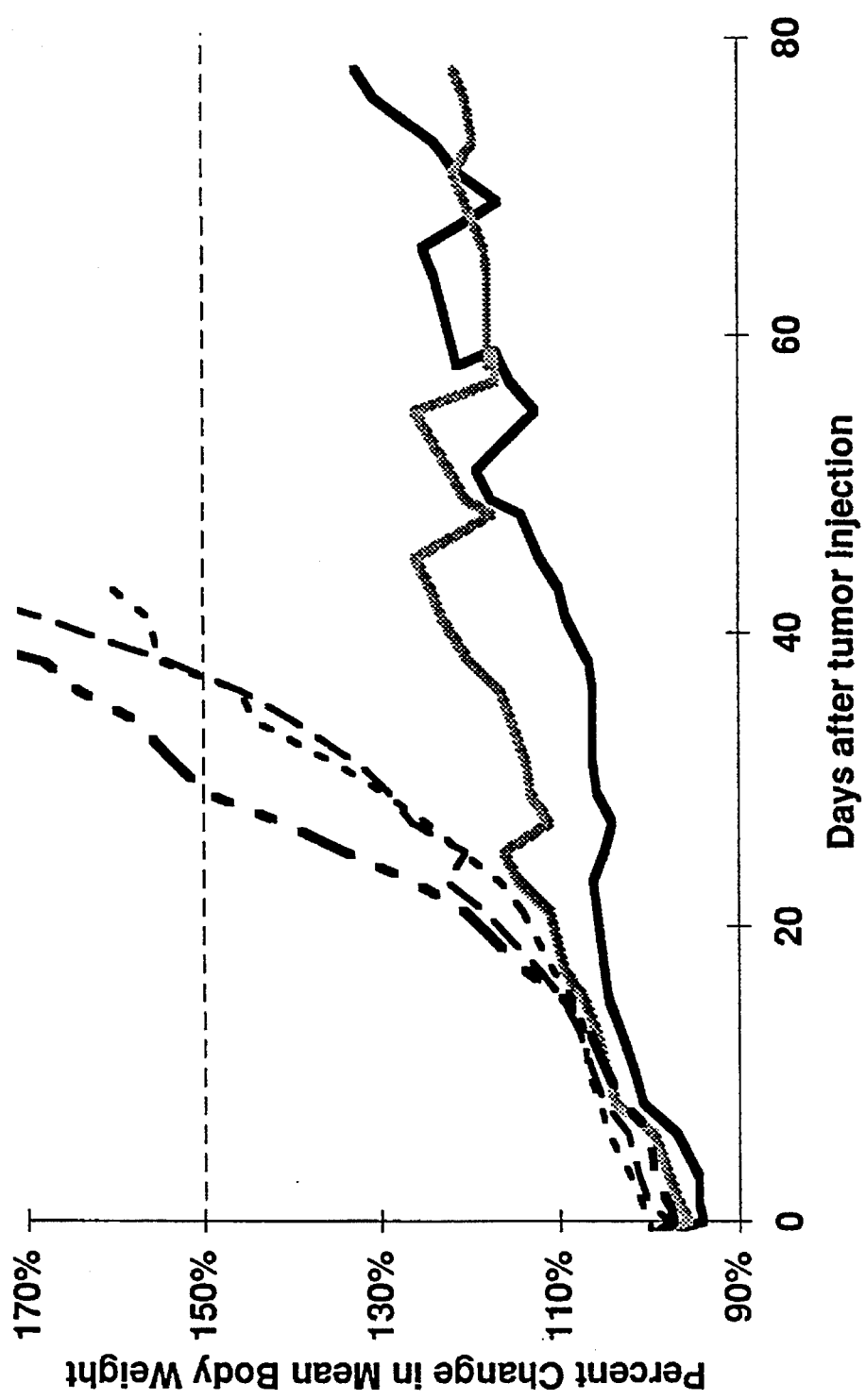

METHOD FOR REDUCING UNWANTED CELLULAR ADHESIONS

BACKGROUND OF THE INVENTION

The present invention relates to a method for placement of therapeutic agents so as to reduce unwanted cellular adhesions. Unwanted cellular adhesions may include, but are not restricted to, adhesions between tumor cells and other tumor cells, adhesions between tumor cells and normal cells, and certain adhesions between normal cells and other normal cells.

Tumor cells are found in two distinct modes: as ascites (free floating cells) and as solid tumors (attached/adhered to host tissue/organs as well as to other tumor cells). Prevention of tumor cell adhesion and growth is a major clinical problem. The control of local tumor recurrence after surgical removal of malignancies is an especially serious concern. The observation that tumor growth occurs at the incision site, even at histopathologically "clean" margins, has led to the conclusion that viable tumor cells have higher affinity for damaged tissue than for normal tissue. This represents one particularly critical aspect of a much broader issue concerning prevention and control of unwanted cellular adhesions. For instance, in cases involving surgical intervention in the abdominal cavity for conditions such as inflammatory bowel disease or endometriosis, there is often the complication of postsurgical adhesions of normal tissue to the resected areas, in a manner similar to that of tumor cell adhesion and colonization or invasion of the wound.

In addition to clinical observations, experimental models of tumor cell adhesion have likewise demonstrated that damaged tissue is an attractive site for tumor growth after systemic injection of viable tumor cells. See, for example, S. Murthy and E. Scanlon, eds., Injury and Tumor Implantation: Biological Mechanisms and Clinical Implications for Recurrence and Metastasis. R.G. Landes Co., Austin, Tex. 1993. It has been reported that specific adhesion molecules and their recognition molecules (receptors) play a role between tumor cell and endothelial cells or extracellular matrix attachment. B. Zetter, Seminars in Cancer Biology, 4: 219–229 (1993). There is a growing list of families of adhesion molecules which are expressed by tumor cells and are stimulated by various environmental conditions or factors, e.g., cytokines.

More recently, there has been a report of evidence showing that display of the receptors or adhesion molecules requires intracellular components known as cytoskeletal elements. F. Pavalko and C. Otey, Proc. Society Exp. Biol. Med., 205: 282–293 (1994); D. Tang, et al., Cancer Res. 54:1119–1129 (1994).

The cytoskeleton is composed of microtubules and various filaments of self-assembling polymers of proteins including tubulin, vimentin, and actin. Adhesion molecules allow communication between the cytoplasmic domains and the cytoskeleton triggering a variety of cellular functions including cell-cell interactions, cell motility and receptor-ligand interactions and receptor internalization. See F. pavalko and C. Otey, supra. Thus, agents which interfere with or disrupt the assembly of microtubules or microfilaments can prevent or inhibit the expression of specific adhesion molecules on cells thereby blocking their recognition, binding, attachment and migration into wounded and healing, or normal tissue.

Colchicine is an agent which binds to tubulin and causes depolymerization of microtubules. Treatment of tumor cells with colchicine has been shown to decrease their ability to bind to lymphatic tissue. See, for example, S. Islam et al., Surgery 113: 676–82 (1993). Treatment of endothelial cells with colchicine likewise blocked tumor cell binding to specific adhesion molecules, as reported by D. Tang, et al., supra. Therefore, microtubule disrupting agents, which are often used in combination regimens for cancer therapy may act not only as cytostatic agents but also as anti-adhesives and possibly as anti-migratory agents thereby decreasing tumor dissemination and metastatic spread.

It has been proposed to reduce the occurrence of adhesion formation resulting from chemotherapeutic treatments involving cisplatin and bleomycin by administering these chemotherapeutic agents in combination with a vinca alkaloid substance, such as vindesine. R. Molloy et al., Irish J. Med. Sci., 159 (6): 175–77 (1990). However, no technique is provided for site specific delivery of the proposed chemotherapeutic combination.

Another approach to controlling unwanted cellular adhesions has been the use of physical barriers, including both mechanical and viscous solutions. See, for example, U.S. Pat. No. 5,250,516. Such barriers tend to prevent adhesion formation by limiting tissue apposition during the critical stages of mesothelial repair. Although use of physical barriers for preventing adhesion formation has been reasonably extensive, general acceptance is constrained because of technical difficulties.

In co-pending U.S. patent application Ser. No. 884,432, which is commonly owned with the present application, there are described various conjugates comprising a therapeutic agent or drug and a lipophilic cell binding agent, in the form of cyanine dyes substituted with relatively long hydrocarbon "tails". These conjugates are capable of stably binding to the lipid regions of cell membranes, thus enabling site selective delivery of therapeutic agents, either via local in vivo administration, e.g., by injection, or by means of a carrier, for retention at the disease site.

The above-noted conjugates afford a number of distinct advantages, as compared with compositions and methods currently available for delivery of therapeutic agents to disease sites. Most notably, the above-mentioned conjugates can be delivered and retained at a selected site in the body by stable association with cell structures at that site. Existing modes of delivery either are unable to deliver sufficient dosages to the disease site without adverse systemic side effects, or are unable to allow sufficient retention of the therapeutic agent at the disease site for a time and in an amount sufficient to produce the desired therapeutic effect.

Moreover, since the lipid regions comprise the majority of the outer membrane of the cell, it is possible to place larger numbers of lipid binding conjugates, and thus a greater concentration of therapeutic agent, into the plasma membrane. Furthermore, because the above-mentioned conjugates are stably incorporated into membrane lipids due to their hydrophobic tails, they are effectively trapped there and cannot dissociate easily. Consequently, leakage from the cells is minimized, thereby reducing undesired systemic effects.

Ongoing research involving the above-mentioned conjugates has led to the discovery of a solution to the problem of reducing unwanted cellular adhesion. When appropriately constituted and utilized, these conjugates can effectively reduce unwanted adhesions, such as: tumor cells to surgical wounds, tumor cells to normal tissue, tumor cells to tumor cells, normal cells to normal cells as in the case of surgical adhesion.

SUMMARY OF THE INVENTION

In accordance with one aspect of the present invention there is provided a method for reducing undesired cell adhesions at a compromised site. The method involves treating the compromised site with a composition comprising a conjugate of a drug and a cell binding agent in an amount effective to inhibit attachment to said site of cells susceptible to unwanted adhesion. The conjugate has the formula

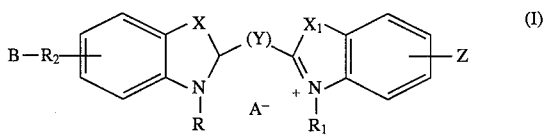

wherein B represents a drug having an inhibitory effect on unwanted cellular adhesions and R and $R_1$ in the cell binding agent represent hydrocarbon substituents having from 1 to about 30 carbon atoms;

X and $X_1$ in the cell binding agent may be the same or different and represent O, S, $C(CH_3)_2$ or Se;

Y in the cell binding agent represents a linking group selected from $=CR_8—,=CR_8—CR_8=CR_8—$, $=CR_8—CR_8=CR_8—CR_8=CR_8—$, or $=CR_8—CR_8=CR_8—CR_8=CR_8—CR_8=CR_8—$, wherein $R_8$ is selected from H, $CH_3$, $CH_2CH_3$, $CH_2CH_2CH_3$ or $CH(CH_3)_2$;

Z in the cell binding agent represents a substituent selected from the group H, alkyl, OH, —O—alkyl, COOH, $CONH_2$, $SO_3H$, $SO_2NH_2$, SH, S-alkyl, CONH-alkyl, CON-(alkyl)$_2$, NH-acyl, NH-alkyl, N(alkyl)$_2$, $NO_2$, halogen, Si(alkyl)$_3$, O—Si(alkyl)$_3$, Sn(alkyl)$_3$ or —Hg—halogen, the alkyl groups comprising the Z substituent having from 1 to 4 carbon atoms;

$R_2$ represents a linking moiety which may comprise one or more functional groups and which links the drug to the cell binding agent; and $A^-$ represents a pharmaceutically acceptable anion.

According to another aspect of this invention, a method for enhancing tumor margin definition is provided which comprises contacting the region of the tumor growth with a composition comprising a drug-cell binding agent conjugate having the formula I, above, which has also been discovered to exhibit a tumor margin definition enhancing effect.

In carrying out the methods of the invention summarized above, the conjugate is conveniently applied to the intended site or region in the form of an irrigation solution.

The methods of the present invention provide a distinct advantage with respect to convenience of use, as compared to existing barrier materials, e.g., physiologically compatible screens, strips and the like, which are used to provide a protective layer at wound repair sites thereby to prevent the occurrence of adhesion.

In addition to reducing cellular adhesions, the compositions of the invention may have a cytostatic or cytotoxic effect on treated cells, or may enhance their sensitivity to x-rays.

Moreover, the affinity of the conjugate for membranes of cell at the site of application effectively "links" the conjugate to that site, so as to minimize any deleterious systemic effect.

Additional advantages and features of the present invention are set forth in, and will be apparent to those skilled in the art from the detailed description of the invention presented below considered in conjunction with the accompanying drawings.

BRIEF DESCRIPTION OF THE DRAWINGS

FIG. 2A is a graphical illustration showing tumor growth (body weight increase) as a function of time elapsed after tumor transplantation for test animals bearing transplanted tumors that were treated after tumor transplantation with the same conjugates, carrier and drug referenced in FIG. 1A.

FIG. 2B is a graphical illustration showing tumor growth (body weight increase) as a function of time elapsed after tumor transplantation for test animals bearing transplanted tumors that were treated before tumor transplantation with the same conjugates, carrier and drug referenced in FIG. 1A, as well as the unconjugated cell binding agent.

DETAILED DESCRIPTION OF THE INVENTION

Figure 1A:
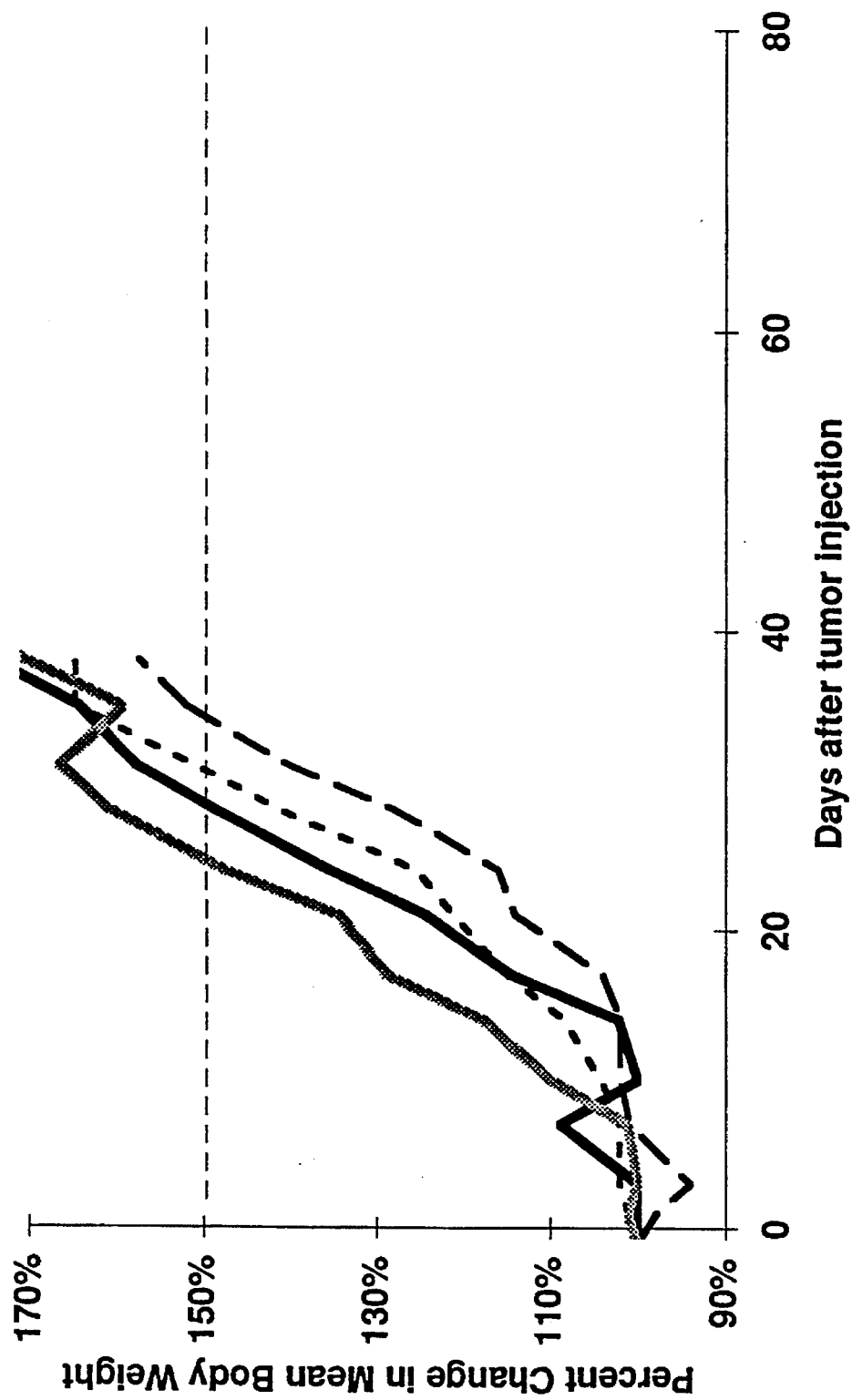
FIG. 1A is a graphical illustration showing tumor growth (body weight increase) as a function of time elapsed after tumor transplantation for test animals bearing transplanted tumors that were treated after tumor transplantation with certain preferred drug-cell binding agent conjugates in comparison to the conjugate carrier alone and the unconjugated drug.

The expression "compromised site" as used herein, refers to a site of a human or animal body at which an environment exists that tends to foster unwanted cell adhesions. Such an environment may exist as a result of surgery, injury, disease, chemotherapy, inflammation or other condition jeopardizing cell viability or function.

Compromised sites are beneficially treated with a composition of the invention comprising a conjugate of formula I, above, in order to reduce adhesion formation. Conjugates of Formula I, above, which are used in the practice of this invention can be prepared according to the synthetic routes described in the above-mentioned U.S. patent application Ser. No. 884,432, the entire disclosure of which is incorporated by reference in the present specification as if set forth herein in full.

These conjugates reduce the occurrence of undesired cell adhesion due to the action of the drug incorporated therein, which may inhibit undesired cell adhesion in several ways. Thus, the drug may act to i) prevent the display of specific adhesion molecules on the cell surface; ii) prevent the intracellular signaling in the cells susceptible to undesired adhesion subsequent to the binding of the adhesion molecules which leads to their further attachment to extracellular matrix, basement membrane, or to normal tissue cells; iii) prevent the release of mediators which stimulate the display of specific adhesion molecules on the surfaces of cells susceptible to undesired adhesion, thereby facilitating the adhesion of cells to cells or tissue to tissue in an unnatural or undesired way; or iv) interfere with the binding of the cell adhesion molecules of one cell to those of another cell or to extracellular matrix proteins contained in the tissue by providing a false or competing substrate.

The drug component of the conjugate is preferably selected from the group of anti-microtubule agents, such as colchicine or vinca alkaloids (e.g., Vinblastine or Vincristine); anti-filament agents, such as cytochalasins B and D or acrylamide or cycloheximide; anti-signaling agents, such as protein kinase C inhibitors, including calphostin, or inhibitors of intracellular calcium mobilization, including 1—O—hexadecyl-2—O—acetyl—SN—glycerol, 8-(diethylamino)octyl-3,4,5-trimethoxybenzoate-HCl or EGTA (ethyleneglycol-bis-(beta-aminoethylether)-N,N,N',N'-tetraacetic acid); inhibitors of release of stimulatory mediators or antagonists of these mediators, such as interleukin 1, transforming growth factor-beta, or 12—S—hydroxyeicosatetraenoic acid, as well as nonsteroidal anti-inflammatory drugs, including ibuprofen and indomethacin; lipoxygenase inhibitors, such as NDGA (nordinhydroguariaretic acid) or Balcalein (5,6,7-trihydroxyflavone); antagonists of release of stimulatory mediators, such as prostacyclin analogue PGI2 (Iloprost®); interleukin-1 receptor antagonist; or other agents effective to interfere with binding of adhesion molecules to their ligands, including the ligands themselves or fragments thereof, such as fibronectin or laminin, or the sequences specific to the binding sites containing the amino acids, arg-gly-glu or tyr-ile-gly-ser-arg, or a combination of such drugs.

Particularly good results have been obtained using conjugates of the following formulae, as will appear from the examples set forth below:

As noted above, "unwanted cellular adhesion" refers to adhesions between tumor cells and other tumor cells, adhesions between tumor cells and normal cells, and certain adhesions between normal cells and other normal cells. Thus, cells susceptible to undesired adhesion include any malignant cells or extracellular matrix generated by malignant cells; normal tissue cells, including endothelial cells, endometrial cells, mesothelial cells or epithelial cells that become injured or inflamed, e.g., as a result of surgical intervention; and signaling or mediator releasing cells including the platelets, macrophages, lymphocytes, or neutrophils. The term "unwanted cell adhesion" does not include the adhesion of cells that occurs in the course of forming normal, healthy tissue.

The expression "enhanced tumor margin definition", as used herein, is intended to signify reduction in fractional area of tumor cells or tumor masses adhering to non-neoplastic tissue or organs, or the tendency of malignant cells to invade normal tissue.

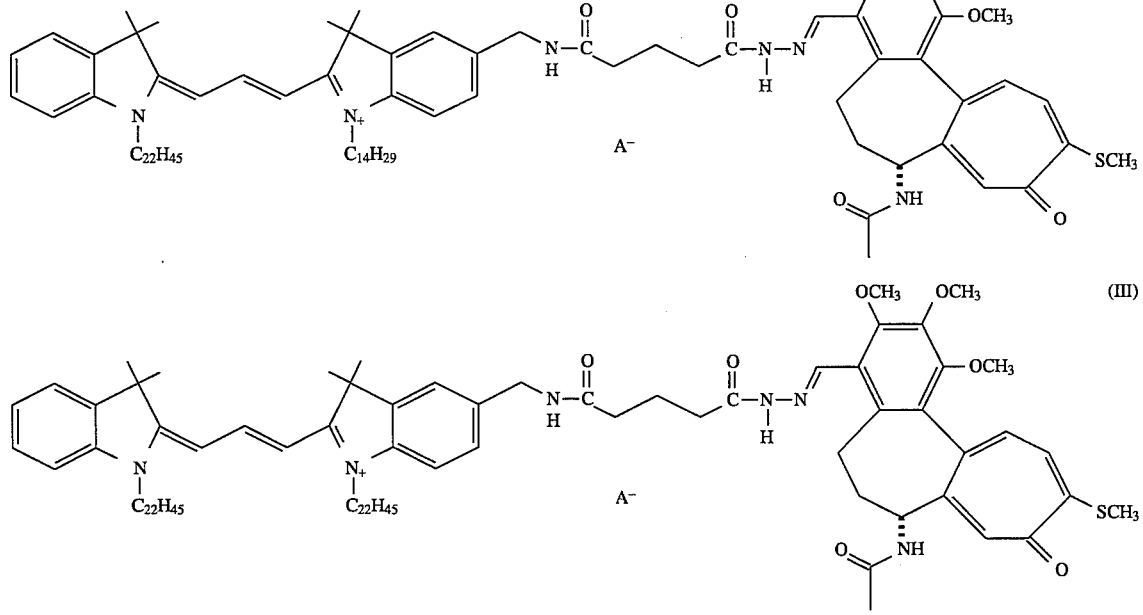

The conjugates described above function like pro-drugs, with the drug being linked to the lipophilic cell binding agent through a cleavable linkage, and exerting its therapeutic effect upon release from the conjugate. Cleavage of the linking moiety is believed to occur after binding and is accelerated by a reduction in pH which promotes disruption of chemical bonds within the linking moiety.

These conjugates release an analogue of colchicine, a molecule which binds to tubulin protein in such a way as to prevent the intracellular functioning of microtubules. These functions include but are not limited to the translocation of cell adhesion molecules to the cell membrane and also the intracellular signaling triggered by binding at the outer cell membrane of these adhesion molecules to their respective ligands.

The conjugates described herein may be conveniently formulated as an irrigation solution in admixture with a biologically compatible carrier, such as dimethylsulfoxide, polyoxyethylene (20) sorbitan monooleate (e.g., Tween-80), polyols, e.g., propyleneglycol, aqueous dextrose (5%) solution, Ringer's solution, saline solution or a combination of such carriers. Concentration of the conjugate in the selected liquid carrier should normally be from about 5 µM to about 5 mM. Where appropriate, the action of contaminating microorganisms can be prevented by various anti-bacterial and anti-fungal agents, such as parabens, chlorobutanol, phenol, sorbic acid, thimerosal and the like. It will often be preferable to include with the conjugate isotonic agents, for example, glucose or sodium chloride.

As used herein, the term "biologically compatible carrier" includes any and all vehicles, solvents, dispersion medium, anti-bacterial and antifungal agents, isotonic agents and the like. The use of such media and agents with therapeutically active substances is known in the art. Except insofar as any conventional media or agent is incompatible with the conjugates described herein, its use in practicing the methods of the present invention is contemplated.

Certain adjuvants, i.e., agents that enhance the effectiveness of the treatment for reducing undesired cell adhesions, may also be used in conjunction with the above-described conjugates, if necessary or desirable. Suitable adjuvants include anti-inflammatories, e.g., non-steroidal, anti-inflammatory drugs (NSAIDs), biological response modifiers, e.g., IL-1 antagonists, or a combination of such adjuvants.

The method of the invention may be used to reduce undesired cell adhesions in connection with surgical intervention for the treatment of cancer in various body cavities or organs where the cancer is found to exist, such as the abdominal cavity, the abdominopelvic cavity, the thoracic cavity, including the pleura and pericardium, the dorsal cavities, including the cranial and spinal cavities, joint cavities, i.e., the space between articulating bones in a synovial joint; lumina, such as the interior of the gastrointestinal tract or a blood vessel, or the female reproductive system. In addition to natural cavities, it is within the contemplation of the present invention to treat induced cavities, i.e., those created by surgical intervention, by the methods described herein. The method may also be advantageously applied to reduce post-surgical adhesions of normal tissue to the wound repair site, such as occurs in connection with surgical intervention for conditions such as inflammatory bowel disease or endometriosis.

Treatment of the surgical site prior to attachment of cells susceptible to undesired adhesion can normally be effected by applying the conjugate prior to, during or immediately after the surgical event. In this way, the well-being of normal tissue in the vicinity of the surgical site can best be preserved.

EXAMPLES

The following examples are provided to describe the invention in further detail. These examples are intended to illustrate and not to limit the invention. Unless otherwise indicated, all reagents and drugs were acquired from Sigma, St. Louis, Mo.

EXAMPLE 1

Pretreatment of Mice Receiving Human Ovarian Carcinoma Cells, i.p. with Thiocolchicine-Conjugated to Lipophilic Cell Binding Agents Pretreatment of mice before introduction of tumor burden was carried out to determine the change in pharmacokinetics of the thiocolchicine analogue, as such, and as conjugated to cell binding agents and having the formulas II and III, respectively, as set forth above. Whereas 4-formyl-thiocolchicine (product of Zynaxis, Inc., Malvern, Pa.) had been experimentally determined to have little or only modest effects on tumor growth when introduced after tumor to the peritoneal cavity of mice bearing human ovarian carcinoma cells, the conjugate of formula II had a more pronounced effect.

In that earlier experiment (A) mice, nu/nu, 5 per group were injected with $5 \times 10^6$ A2780 human ovarian carcinoma cell (i.p.) and treated the following day with the compound(s) listed in Table 1, below. Median survival day was the average day of death of the second and third test animal. As can be seen from the data in Table 1, the increase in life span (% ILS) of mice treated with 4-formyl-thiocolchicine ((S)—N—[5,6,7,9-tetrahydro-1,2,3-trimethoxy-4-formyl-10-(methylthio)-9-oxobenzo[a] heptalen-7-yl] acetamide; $C_{23}H_{25}NO_6S$) was 10%, which was significantly different from the 10% DMSO treated group ($p \leq 0.05$). Both groups treated with the conjugate of formula II had significantly longer survival times than those treated with 4-formyl-thiocolchicine group ($p \leq 0.01$). The survival time of mice treated with the conjugate of formula II was not different than those treated with 500 nmol of Cisplatin.

The compounds listed in Table 1, including 4—F—T, produced no observable adverse effects at any of the concentrations tested.

TABLE 1

| Compound(s) | Dose nmol per mouse | Day Treated | Median Survival (D) | % ILS |
|---|---|---|---|---|
| Experiment A: | | | | |
| 10% DMSO | — | +1 | 43 | — |
| Cisplatin (4.5 mg/kg) | 250 | +1 | 45 | 5 |
| Cisplatin (9.0 mg/kg) | 500 | +1 | 52 | 20 |
| 4-F-T[a] | 500 | +1 | 48 | 10 |
| 4-F-T + CBA[b] | 500 + 500 | +1 | 44 | 2 |
| Formula II Conjugate | 250 | +1 | 51 | 17 |
| Formula II Conjugate | 500 | +1 | 53 | 22 |

[a]4-formyl-thiocolchicine
[b]cell binding component of formula II, above

Previous pharmacokinetics studies in other models showed rapid disappearance and/or metabolism of 4-formyl-thiocolchicine. Therefore, a pretreatment protocol was designed to determine the longevity of efficacy.

In carrying out the protocol (experiments B and C), the human ovarian line, A2780 (gift of T. C. Hamilton of Fox Chase Cancer Center, Phila., Pa.), was maintained in tissue culture (RPMI 1640 Bio-Whittaker, Walkersville, Md.), with 10% fetal bovine serum (GIBCO) and 0.26 u/m/bovine insulin (GIBCO). For tumor initiation, $5 \times 10^6$ cells were injected i.p. into NIH: Balb/C nu/nu female mice five per group. Two types of treatment schedules were performed, a single i.p. injection on the day before the tumor cells were implanted or a single i.p. injection on the day after tumor cells were implanted.

Syntheses of 4-formyl-thiocolchicine and the conjugates of formulas II and III were performed at Zynaxis, Inc., Malvern, Pa., utilizing the synthetic routes described in the above-mentioned U.S. patent application Ser. No. 07/884, 432. These compounds were shown to be greater than 95% pure by HPLC and NMR and/or mass spectroscopy.

The dosing levels of the compounds were calculated in terms of molar equivalents to assure that the therapeutic concentration was uniform across groups. Compounds were first dissolved in dimethylsulfoxide (DMSO) and administered in 0.5 ml of a maximum of 10% DMSO in water. No toxicity symptoms were noted at the administered dose which was 500 nmol per mouse.

Efficacy was monitored by the change in group mean body weight and scored as increase in median survival time of treated versus the controls which were given carrier only (10% DMSO).

Two identical protocols were run at two different facilities. The protocols were identical except that the source of mice for experiment B was the NCI, Frederick, Md. and for experiment C the mice were provided by Jackson Laboratory, Bar Harbor, Me. Experiment C also contained the additional control group of mice treated with cell binding agent, as such, i.e. free of any conjugated therapeutic agent. In experiment C, mice were sacrificed when the tumor burden exceeded 75% of initial body weight for humane reasons.

Kaplan-Meier statistics were calculated using the comparing pairs of groups using the Wilcoxon test.

The results of these two experiments are set forth, in part, in FIGS. 1A, 1B, 2A and 2B, wherein the dotted line (...) represents a 10% solution of DMSO in water; the dashed line (---) represents 4-formylthiocolchicine; the solid line (___) represents the conjugate of formula II, above; and the stipled line (⌇⌇⌇) represents the conjugate of formula III, above.

Figure 1B:
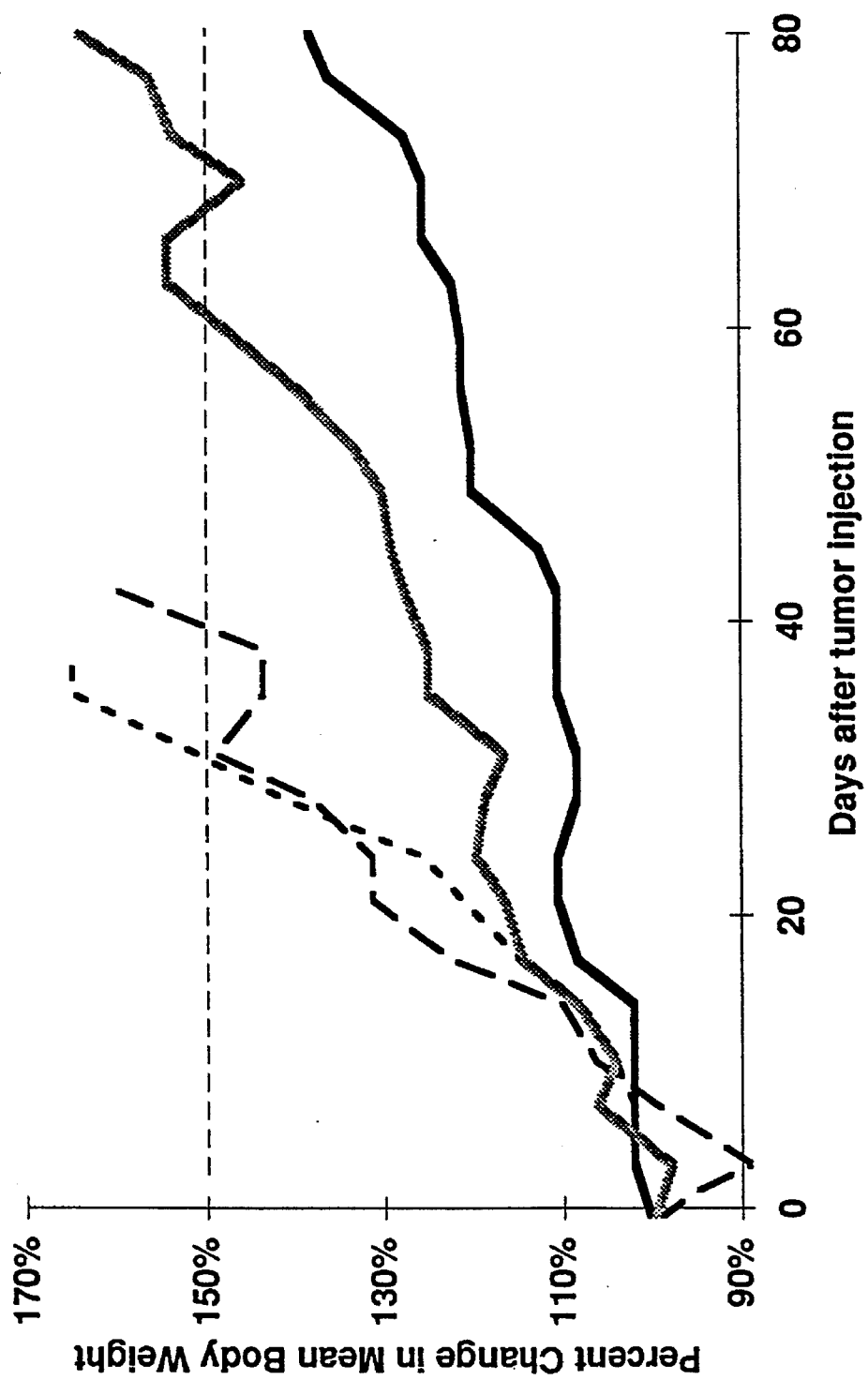
FIG. 1B is a graphical illustration showing tumor growth (body weight increase) as a function of time elapsed after tumor transplantation for test animals bearing transplanted tumors that were treated before tumor transplantation, using the same conjugates, carrier and drug referenced in FIG. 1A.

The effect of pretreatment was to prevent the increase in body weight of the mice associated with the tumor growth, as can be seen from the data in FIGS. 1A and 1B, which set forth data resulting from experiment B. In that experiment, the delay in tumor growth for mice pretreated with either of the conjugates of formula II or III was evident. In particular, FIG. 1B shows that the effect of pretreatment was to prevent the increase in body weight of the mice associated with the tumor growth as seen in all the groups treated one day after tumor cells had been injected. (Compare FIG. 1A).

The results of experiment C were similar to those obtained in experiment B, in that pretreatment with the conjugates of formula II and III delayed tumor growth. These results are set forth in FIGS. 2A and 2B. Little or no effect was seen from posttreatment with either conjugate; nor did the nonconjugated therapeutic agent or the nonconjugated cell binding agent alone have any effect on total tumor burden.

Time to reach 150% of initial body weight was derived from the above described figures and is shown in Tables 2 and 3, below, along with the median survival time or day of sacrifice for each group. All of the groups of mice pretreated with the conjugates of formula II and III had significantly longer survival times or times of low tumor burden, as compared with mice treated with unconjugated 4-formyl-thiocolchicine, or unconjugated cell binding agent, before tumor injection, or after tumor injection. As can be seen from the data in Tables 2 and 3, posttreatment produced no appreciable effect on the survival time of mice given either conjugated or unconjugated thiocolchicine analogue. By contrast, pretreatment with the conjugates of formula II and III caused a marked prolongation of life span.

TABLE 2

| Compound(s) | Time to Reach 150% of Initial Weight | Day Treated | Median Survival (D) | % ILS |
|---|---|---|---|---|
| 10% DMSO | 30 | +1 | 38 | |
| 4-F-T | 34 | +1 | 40 | 4 |
| Formula II Conjugate | 28 | +1 | 42 | 9 |
| Formula III Conjugate | 25 | +1 | 39 | 3 |

TABLE 2-continued

| Compound(s) | Time to Reach 150% of Initial Weight | Day Treated | Median Survival (D) | % ILS |
|---|---|---|---|---|
| 4-F-T | 30 | −1 | 37 | −4 |
| Formula II Conjugate | >80 | −1 | >120* | >200 |
| Formula III Conjugate | 60 | −1 | >104* | >173 |

*These groups each had 3/5 animals which survived more than 120 days.

TABLE 3

| Compound(s) | Time to Reach 150% of Initial Weight | Day Treated | Median Day of Sacrifice | % ILS |
|---|---|---|---|---|
| 10% DMSO | 36 | +1 | 43 | |
| 4-F-T | 32 | +1 | 45 | 5 |
| Formula II Conjugate | 36 | +1 | 44 | 2 |
| Formula III Conjugate | 43 | +1 | 45 | 5 |
| 4-F-T | 35 | −1 | 33 | −24 |
| Formula II Conjugate | >80 | −1 | 61 | 41 |
| Formula III Conjugate | >80 | −1 | 52 | 21 |
| CBA[a] | 28 | −1 | 36 | −17 |

[a]Cell binding agent of formula III, above.

Although the survival times are different in experiments B and C, it should be noted that the mice were sacrificed when they reached 35 g (175% of initial body weight) in experiment C rather than allowing them to succumb to tumor burden. The time to reach 150% body weight, however, indicates that the animals pretreated with the formula III conjugate in experiment C had better tumor control than did the animals in experiment B treated the same way since the time increased from 60 days to >80 days.

In addition to body weight change and time to 175% of initial body weight change, animals in experiment C were necropsied and gross pathology was performed. It was observed that the tumor pathogenesis in mice treated either with vehicle control, with 4-formyl-thiocolchicine or with the cell binding component of the conjugate of formula III had widely disseminated tumor covering all surfaces of the peritoneum, the organs and often the lower surface of the diaphragm. Mice treated with the conjugates of formulas II or III, whether pre or post tumor injection, had more focal lesions (i.e., enhanced tumor margin definition) though large masses had formed by the time of sacrifice.

The data resulting from the above-described experiments tend to establish that pretreatment of the peritoneal cavity with the conjugates described above has an effect which cannot be explained as simple decrease in early stage tumor cell number. For the difference between tumor cell number at day 0 and 1 day thereafter will not be greater than a factor of two given the tumor cell doubling time of 22 hours. Thus, the observed effect can be attributable to alteration of the "bed" in terms of the epithelial and endothelial cells and the "environment" of the cavity. By this is meant the cytokine and adhesion molecule balance at the site where the undesired cells may bind. The over 60 different cytokines identified thus far can be variously categorized, depending on whether they are immunomodulatory, inflammatory, chemoattractant or growth regulatory. The three former types can lead to increased adhesion molecule expression and activation and therefore increased cell binding. See, for example, A. Thompson, The Cytokine Handbook, 2nd Edition, Academic Press, 1994 and J. Harlan and D. Liu, Adhesion: Its role in Inflammatory Disease. W.H. Freeman and Co., New York, 1992.

The fact that the pathogenesis of the disease was altered in such a way as to produce an operable situation with well defined margins demonstrates the advantage of treating the compromised site prior to attachment of cells susceptible to undesired adhesion. Furthermore, it is believed that treatment of a compromised site soon after attachment of cells susceptible to unwanted adhesions will be similarly effective.

While certain embodiments of the present invention have been described and/or exemplified above, various other embodiments will be apparent to those skilled in the art from the foregoing disclosure. For example, the conjugates described herein may be attached, e.g., via adsorption, to a biomaterial, such as barrier materials used for protection of wound repair sites, suture materials and the like, prior to the insertion of that biomaterial into a body cavity, thereby providing enhanced prevention of unwanted cellular adhesion by the biomaterial. The present invention is, therefore, not limited to the particular embodiments described and/or exemplified, but is capable of considerable variation and modification without departure from the scope of the appended claims.

What is claimed is:

1. A method for reducing unwanted cell adhesion at a compromised site comprising treating said site with a composition comprising a conjugate of a drug and a cell binding agent, in an amount effective to inhibit attachment to said site of cells susceptible to unwanted adhesion, said conjugate having the formula:

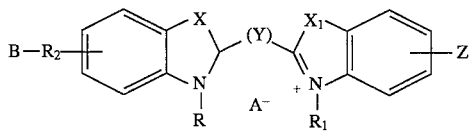

wherein B represents a drug having an inhibitory effect on cell adhesion and R and $R_1$ in said cell binding agent represent hydrocarbon substituents having from 1 to about 30 carbon atoms;

X and $X_1$ in said cell binding agent may be the same or different and represent O, S, $C(CH_3)_2$ or Se;

Y in said cell binding agent represents a linking group selected from $=CR_8-$, $=CR_8-CR_8=CR_8-$, $=CR_8-CR_8=CR_8-CR_8=CR_8-$, or $=CR_8-CR_8=CR_8-CR_8=CR_8-CR_8=CR_8-$, wherein $R_8$ is selected from H, $CH_3$, $CH_2CH_3$, $CH_2CH_2CH_3$ or $CH(CH_3)_2$;

Z in said cell binding agent represents a substituent selected from the group H, alkyl, OH, —O— alkyl, COOH, $CONH_2$, $SO_3H$, $SO_2NH_2$, SH, S-alkyl, CONH-alkyl, CON-(alkyl)$_2$, NH-acyl, NH-alkyl, N(alkyl)$_2$, $NO_2$, halogen, Si(alkyl)$_3$, O—Si(alkyl)$_3$, Sn(alkyl)$_3$ or —Hg— halogen, the alkyl groups comprising said Z substituent having from 1 to 4 carbon atoms;

$R_2$ represents a linking moiety which links said drug to said cell binding agent; and A— represents a pharmaceutically acceptable anion.

2. A method as claimed in claim 1, wherein said drug is conjugated to said cell binding agent via a cleavable linking moiety.

3. A method as claimed in claim 1, wherein said site is compromised by surgery.

4. A method as claimed in claim 1, wherein said site is compromised by inflammation.

5. A method as claimed in claim 1, wherein said site is compromised by injury.

6. A method as claimed in claim 1, wherein said site is compromised by disease.

7. A method as claimed in claim 1, wherein said site is compromised by chemotherapy.

8. A method as claimed in claim 1, wherein said cells susceptible to unwanted adhesion are selected from the group of malignant cells, inflammatory cells, diseased cells, chemotherapeutically-treated cells or injured normal cells.

9. A method as claimed in claim 1, wherein said compromised site is the abdominal cavity.

10. A method as claimed in claim 1, wherein said compromised site is the thoracic cavity.

11. A method as claimed in claim 1, wherein said compromised site is the pleural cavity.

12. A method as claimed in claim 1, wherein said compromised site is the pericardial cavity.

13. A method as claimed in claim 1, wherein said compromised site is a joint cavity.

14. A method as claimed in claim 13, wherein said joint is a synovial joint.

15. A method as claimed in claim 1, wherein said compromised site is the female reproductive system.

16. A method as claimed in claim 1, wherein said compromised site is treated with a composition comprising the conjugate of claim 1, wherein said drug is selected from the group consisting of anti-microtubule agents, anti-filament agents, anti-signaling agents, inhibitors of release of stimulatory mediators, inhibitors of antagonists of stimulatory mediators, antagonists of release of stimulatory mediators and agents effective to interfere with binding of adhesion molecules to their respective ligands.

17. A method as claimed in claim 1, wherein said composition further comprises a biologically compatible carrier.

18. A method as claimed in claim 17, wherein said carrier is selected from the group consisting of dimethyl sulfoxide, polyoxyethylene sorbitan mono-oleate, polyols, aqueous dextrose solution, Ringer's solution, saline solution, or a combination of said carriers.

19. A method as claimed in claim 1, wherein said composition further comprises an adjuvant.

20. A method as claimed in claim 19, wherein said adjuvant is selected from the group consisting of anti-inflammatory agents, biological response modifiers or a combination of said adjuvants.

21. A method as claimed in claim 1, wherein said composition comprises a conjugate of the formula

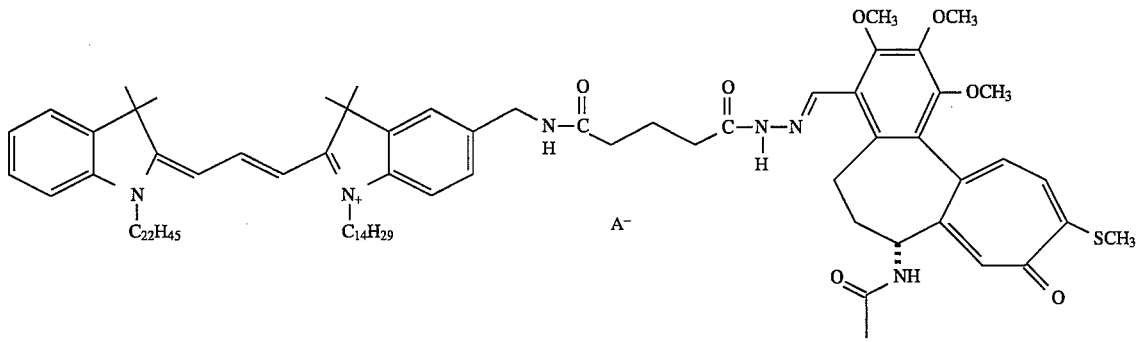

wherein A— represents a pharmaceutically acceptable anion.

22. A method as claimed in claim 1, wherein said composition comprises a conjugate of the formula

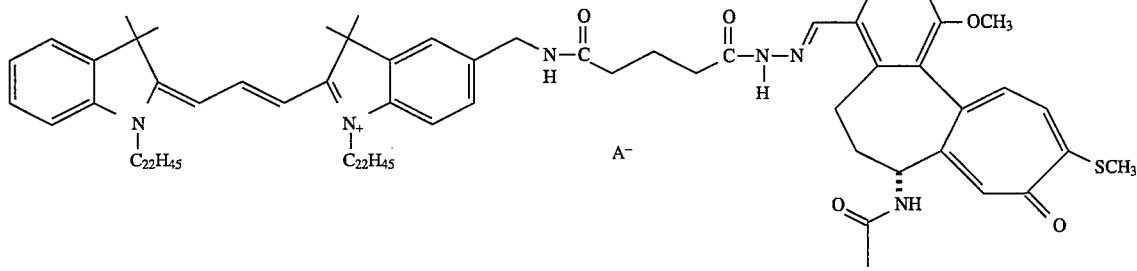

wherein A— represents a pharmaceutically acceptable anion.

23. A method of enhancing tumor margin definition which comprises contacting the region of said tumor with a composition comprising a conjugate of a drug and a cell binding agent having the formula:

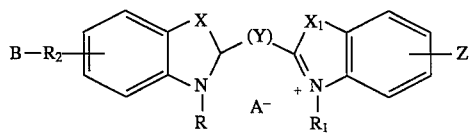

wherein B represents a drug which inhibits cellular expression of adhesion molecules and R and $R_1$ in said cell binding agent represent hydrocarbon substituents having from 1 to about 30 carbon atoms;

X and $X_1$ in said cell binding agent may be the same or different and represent O, S, $C(CH_3)_2$ or Se;

Y in said cell binding agent represents a linking group selected from $=CR_8—, =CR_8—CR_8=CR_8—$, $=CR_8— CR_8=CR_8—CR_8=CR_8—$, or $=CR_8—CR_8=CR_8—CR_8=CR_8—CR_8=CR_8—$, wherein $R_8$ is selected from H, $CH_3$, $CH_2CH_3$, $CH_2CH_2CH_3$ or $CH(CH_3)_2$;

Z in said cell binding agent represents a substituent selected from said group H, alkyl, OH, —O—alkyl, COOH, $CONH_2$, $SO_3H$, $SO_2NH_2$, SH, S—alkyl, CONH-alkyl, CON-(alkyl)$_2$, NH-acyl, NH-alkyl, N(alkyl)$_2$, $NO_2$, halogen, Si(alkyl)$_3$O—Si(alkyl)3, Sn(alkyl)3 or —Hg— halogen, said alkyl groups comprising said Z substituent having from 1 to 4 carbon atoms;

$R_2$ represents a linking moiety which links said drug to said cell binding agent; and A— represents a pharmaceutically acceptable anion, said conjugate being used in an amount effective to enhance tumor margin definition.

24. A method as claimed in claim 23, wherein the region of said tumor is the abdominal cavity.

25. A method as claimed in claim 23, wherein the region of said tumor is the thoracic cavity.

26. A method as claimed in claim 23, wherein the region of said tumor is the female reproductive system.

27. A method as claimed in claim 23, wherein the region of said tumor is the pleural cavity.

28. A method as claimed in claim 23, wherein the region of said tumor is the pericardial cavity.

29. A method as claimed in claim 1, wherein the region of said tumor is a joint cavity.

30. A method as claimed in claim 23, wherein said joint is a synovial joint.

31. A method as claimed in claim 23, wherein said composition further comprises a biologically compatible carrier selected from the group consisting of dimethyl sulfoxide, polyoxyethylene sorbitan mono-oleate, polyols, aqueous dextrose solution, Ringer's solution, saline solution, or a combination of said carriers.

32. An improved biomaterial for emplacement at a compromised site to form a barrier between said site and cells susceptible to unwanted adhesion, the improvement wherein said biomaterial has applied thereto a composition comprising a conjugate of a drug and a cell binding agent, in an amount effective to inhibit attachment to said site of cells susceptible to unwanted adhesion, said conjugate having the formula:

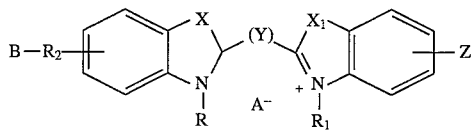

wherein B represents a drug having an inhibitory effect on cell adhesion and R and $R_1$ in said cell binding agent represent hydrocarbon substituents having from 1 to about 30 carbon atoms;

X and $X_1$ in said cell binding agent may be the same or different and represent O, S, $C(CH_3)_2$ or Se;

Y in said cell binding agent represents a linking group selected from $=CR_8—$, $=CR_8—CR_8=CR_8—$, $=CR_8— CR_8=CR_8—CR_8=CR_8—$, or $=CR_8— CR_8=CR_8—CR_8=CR_8—CR_8=CR_8—$, wherein $R_8$ is selected from H, $CH_3$, $CH_2CH_3$, $CH_2CH_2CH_3$ or $CH(CH_3)_2$;

Z in said cell binding agent represents a substituent selected from the group H, alkyl, OH, —O—alkyl, COOH, $CONH_2$, $SO_3H$, $SO_2NH_2$, SH, S—alkyl, CONH-alkyl, CON-(alkyl)$_2$, NH-acyl, NH-alkyl, N(alkyl)$_2$, $NO_2$, halogen, Si(alkyl)$_3$, O—Si(alkyl)$_3$, Sn(alkyl)$_3$ or —Hg— halogen, the alkyl groups comprising said Z substituent having from 1 to 4 carbon atoms;

$R_2$ represents a linking moiety which links said drug to said cell binding agent; and A— represents a pharmaceutically acceptable anion.

33. An improved biomaterial as claimed in claim 32, wherein said composition comprises a conjugate of the formula

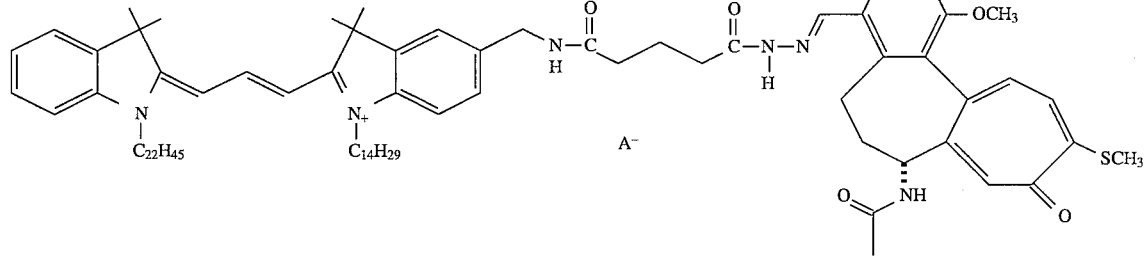

wherein A— represents a pharmaceutically acceptable anion.

34. An improved biomaterial as claimed in claim 32, wherein said composition comprises a conjugate of the formula

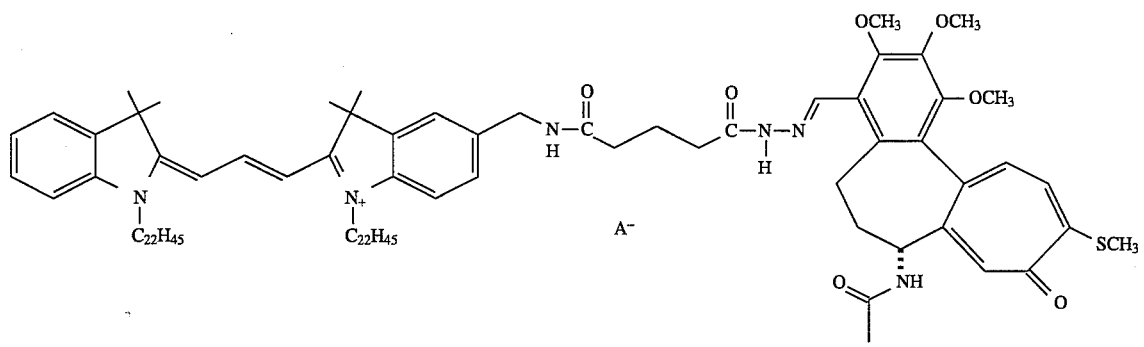
wherein A— represents a pharmaceutically acceptable anion.
* * * * *